(12) United States Patent
Zhang et al.

(10) Patent No.: US 6,891,029 B2
(45) Date of Patent: May 10, 2005

(54) ISOLATED POLYNUCLEOTIDE SEQUENCES ENCODING A FERTILITY ASSOCIATED ANTIGEN

(75) Inventors: Huanmin Zhang, Tucson, AZ (US); Roy L. Ax, Tucson, AZ (US); Mary E. Bellin, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 248 days.

(21) Appl. No.: 09/905,114

(22) Filed: Jul. 16, 2001

(65) Prior Publication Data

US 2002/0048745 A1 Apr. 25, 2002

Related U.S. Application Data

(60) Provisional application No. 60/218,140, filed on Jul. 14, 2000.

(51) Int. Cl.[7] .......... C07H 21/04; C12N 15/63; C12N 15/09; C12N 15/74; C12N 5/00
(52) U.S. Cl. .......... 536/23.5; 435/320.1; 435/69.3; 435/455; 435/471; 435/325
(58) Field of Search .......... 536/23.1, 23.2, 536/23.5; 435/320.1, 69.1, 69.3, 455, 471, 325

(56) References Cited

U.S. PATENT DOCUMENTS

| 5,693,496 A | 12/1997 | Alves et al. | 435/69.3 |
| 5,962,241 A | 10/1999 | Ax et al. | 435/7.92 |

OTHER PUBLICATIONS

Baron et al. Cloning and characterization of an actin–resistant DNase I–like endonuclease secreted by macrophages. Gene 215:291–301, 1998.*

Salois et al. Complementary deoxyribonucleic acid cloning and tissue expression of BSP-A3 and BSP-30-kDa: Phosphatidylcholine and heparin-binding proteins of bone seminal plasma. Biol. Reproduction 61:288–297, 1999.*

Rudinger, J. Characteristics of the amino acids as components of a peptide hormone sequence. 1976. In: Peptide Hormones (Parsons, J.A., ed.), University Park Press, Baltimore, pp. 1–7.

Ngo et al. Computational complexity, protein structure prediction, and the Levinthal paradox. 1994. In: The protein folding problem and tertiary structure prediction (Merz et al., eds.); Birkhauser, Boston, pp. 491–495.

Kennell, D.E. Principles and practices of Nucleic acid hybridization. Progr. Nucl. Acid Res. Mol. Biol. 11:259–301, 1971.

McCauley et al., "Purification and Characterization of Fertility–Associated Antigen (FAA) in Bovine Seminal Fluid. Molecular Reproduction and Development" Oct. 1999, vol. 54, pp. 145–153, see entire document.

Bellin et al., Fertility–Associated Antigen on Bull Sperm Indicates Fertility Potential. J. Animal Science. Jul. 1998, vol. 76, pp. 2032–2039, see entire document.

* cited by examiner

*Primary Examiner*—David Guzo
*Assistant Examiner*—Quang Nguyen
(74) *Attorney, Agent, or Firm*—Oblon, Spivak, McClelland, Maier & Neustadt, P.C.

(57) ABSTRACT

The present invention provides an isolated polynucleotide sequence and amino acid sequence for a bovine fertility associated antigen (FAA), methods of producing recombinant bovine FAA protein; methods of increasing the stability of the plasma membrane, acrosome, and/or other portions of a sperm cell by mixing with FAA and/or recombinant FAA protein(s); and increasing fertility of bulls by mixing sperm cells with FAA and/or recombinant FAA protein(s).

14 Claims, 6 Drawing Sheets

```
  1  ACAACAGGAT CTGCCCCATA CTGATGGAGA AGCTAAACGG AAATTCAAGA

51  AAAGGCATAA CATACAACTA TGTGATTAGC TCTCGCCTTG GAAGAAACAC

101  ATATAAAGAA CAGTATGCCT TTCTCTATAA AGAAAAGCTA GTGTCTGTAA

151  AACAAAGCTA CCTCTACCAC GACTATCAGG CTGGAGACGC AGATGTGTTT

201  TCCAGGGAAC CCTTTGTGGT CTGGTTCCAG TCACCCTACA CCGCTGTCAA

251  GGACTTCGTG ATTGTCCCCC TGCACACCAC CCCTGAGACA TCCGTTAGAG

301  AGATTGATGA GCTGGCTGAT GTCTACACAG ATGTGAAACG TCGCTGGAAT

351  GCAGAGAATT TCATTTTCAT GGGTGACTTC AATGCTGGCT GCAGCTACGT

401  CCCCAAGAAG GCCTGGAAGG ACATCCGCCT GAGGACGGAC CCCAAGTTCG

451  TTTGGCTGAT CGGGGACCAA GAGGACACCA CGGTCAAGAA GAGCACAAAC

501  TGCGCCTATG ACAGGATCGT GCTTAGAGGA CAAAATATTG TCAACTCTGG

551  TGGTCCTCAA TCAAACCTCG TCTTTGATTT CCAGAAAGCT TACAGGTTGT

601  CTGAATCGAA GGCCCTGGAT GTCAGCGACC ACTTTCCAGT TCATCATCAT

651  CATCATCATG AAGAACCATG A
```

*FIG. 5*

```
    GAGAAGCTAAACGGAAATTCAAGAAAAGGCATAACATACAACTATGTGATTAGCTCTCGC
5'
  1 ------------+----------+----------+----------+----------+----------+ 60
a   E  K  L  N  G  N  S  R  K  G  I  T  Y  N  Y  V  I  S  S  R    -

CTTGGAAGAAACACATATAAAGAACAGTATGCCTTTCTCTATAAAGAAAAGCTAGTGTCT
 61 ------------+----------+----------+----------+----------+----------+ 120
a   L  G  R  N  T  Y  K  E  Q  Y  A  F  L  Y  K  E  K  L  V  S    -

GTAAAACAAAGCTACCTCTACCACGACTATCAGGCTGGAGACGCAGATGTGTTTTCCAGG
121 ------------+----------+----------+----------+----------+----------+ 180
a   V  K  Q  S  Y  L  Y  H  D  Y  Q  A  G  D  A  D  V  F  S  R    -

GAACCCTTTGTGGTCTGGTTCCAGTCACCCTACACCGCTGTCAAGGACTTCGTGATTGTC
181 ------------+----------+----------+----------+----------+----------+ 240
a   E  P  F  V  V  W  F  Q  S  P  Y  T  A  V  K  D  F  V  I  V    -

CCCCTGCACACCACCCCTGAGACATCCGTTAGAGAGATTGATGAGCTGGCTGATGTCTAC
241 ------------+----------+----------+----------+----------+----------+ 300
a   P  L  H  T  T  P  E  T  S  V  R  E  I  D  E  L  A  D  V  Y    -

ACAGATGTGAAACGTCGCTGGAATGCAGAGAATTTCATTTTCATGGGTGACTTCAATGCT
301 ------------+----------+----------+----------+----------+----------+ 360
a   T  D  V  K  R  R  W  N  A  E  N  F  I  F  M  G  D  F  N  A    -

GGCTGCAGCTACGTCCCCAAGAAGGCCTGGAAGGACATCCGCCTGAGGACGGACCCCAAG
361 ------------+----------+----------+----------+----------+----------+ 420
a   G  C  S  Y  V  P  K  K  A  W  K  D  I  R  L  R  T  D  P  K    -

TTCGTTTGGCTGATCGGGGACCAAGAGGACACCACGGTCAAGAAGAGCACAAACTGCGCC
421 ------------+----------+----------+----------+----------+----------+ 480
a   F  V  W  L  I  G  D  Q  E  D  T  T  V  K  K  S  T  N  C  A    -

TATGACAGGATCGTGCTTAGAGGACAAAATATTGTCAACTCTGGTGGTCCTCAATCAAAC
481 ------------+----------+----------+----------+----------+----------+ 540
a   Y  D  R  I  V  L  R  G  Q  N  I  V  N  S  G  G  P  Q  S  N    -

CTCGTCTTTGATTTCCAGAAAGCTTACAGGTTGTCTGAATCGAAGGCCCTGG          3'
541 ------------+----------+----------+----------+----------+--  592
a   L  V  F  D  F  Q  K  A  Y  R  L  S  E  S  K  A  L             -
```

*FIG. 6*

SEQUENCE LISTING

<160> NUMBER OF SEQ ID NOS: 9

<210> SEQ ID NO 1
<211> LENGTH: 592
<212> TYPE: DNA
<213> ORGANISM: Bos sp.
<220> FEATURE:
<221> NAME/KEY: CDS
<222> LOCATION: (1)..(591)
<223> OTHER INFORMATION:

<400> SEQUENCE: 1

```
gag aag cta aac gga aat tca aga aaa ggc ata aca tac aac tat gtg      48
Glu Lys Leu Asn Gly Asn Ser Arg Lys Gly Ile Thr Tyr Asn Tyr Val
1               5                   10                  15 att agc tct cgc ctt gga aga aac aca tat aaa gaa cag tat gcc ttt      96
Ile Ser Ser Arg Leu Gly Arg Asn Thr Tyr Lys Glu Gln Tyr Ala Phe
                20                  25                  30 ctc tat aaa gaa aag cta gtg tct gta aaa caa agc tac ctc tac cac     144
Leu Tyr Lys Glu Lys Leu Val Ser Val Lys Gln Ser Tyr Leu Tyr His
            35                  40                  45 gac tat cag gct gga gac gca gat gtg ttt tcc agg gaa ccc ttt gtg     192
Asp Tyr Gln Ala Gly Asp Ala Asp Val Phe Ser Arg Glu Pro Phe Val
        50                  55                  60 gtc tgg ttc cag tca ccc tac acc gct gtc aag gac ttc gtg att gtc     240
Val Trp Phe Gln Ser Pro Tyr Thr Ala Val Lys Asp Phe Val Ile Val
65                  70                  75                  80 ccc ctg cac acc acc cct gag aca tcc gtt aga gag att gat gag ctg     288
Pro Leu His Thr Thr Pro Glu Thr Ser Val Arg Glu Ile Asp Glu Leu
                85                  90                  95 gct gat gtc tac aca gat gtg aaa cgt cgc tgg aat gca gag aat ttc     336
Ala Asp Val Tyr Thr Asp Val Lys Arg Arg Trp Asn Ala Glu Asn Phe
            100                 105                 110 att ttc atg ggt gac ttc aat gct ggc tgc agc tac gtc ccc aag aag     384
Ile Phe Met Gly Asp Phe Asn Ala Gly Cys Ser Tyr Val Pro Lys Lys
        115                 120                 125 gcc tgg aag gac atc cgc ctg agg acg gac ccc aag ttc gtt tgg ctg     432
Ala Trp Lys Asp Ile Arg Leu Arg Thr Asp Pro Lys Phe Val Trp Leu
130                 135                 140 atc ggg gac caa gag gac acc acg gtc aag aag agc aca aac tgc gcc     480
Ile Gly Asp Gln Glu Asp Thr Thr Val Lys Lys Ser Thr Asn Cys Ala
145                 150                 155                 160 tat gac agg atc gtg ctt aga gga caa aat att gtc aac tct ggt ggt     528
Tyr Asp Arg Ile Val Leu Arg Gly Gln Asn Ile Val Asn Ser Gly Gly
                165                 170                 175 cct caa tca aac ctc gtc ttt gat ttc cag aaa gct tac agg ttg tct     576
Pro Gln Ser Asn Leu Val Phe Asp Phe Gln Lys Ala Tyr Arg Leu Ser
            180                 185                 190 gaa tcg aag gcc ctg g                                                592
Glu Ser Lys Ala Leu
        195
```

<210> SEQ ID NO 2
<211> LENGTH: 197
<212> TYPE: PRT
<213> ORGANISM: Bos sp.

<400> SEQUENCE: 2

```
Glu Lys Leu Asn Gly Asn Ser Arg Lys Gly Ile Thr Tyr Asn Tyr Val
1               5                   10                  15

Ile Ser Ser Arg Leu Gly Arg Asn Thr Tyr Lys Glu Gln Tyr Ala Phe
                20                  25                  30

Leu Tyr Lys Glu Lys Leu Val Ser Val Lys Gln Ser Tyr Leu Tyr His
            35                  40                  45

Asp Tyr Gln Ala Gly Asp Ala Asp Val Phe Ser Arg Glu Pro Phe Val
        50                  55                  60

Val Trp Phe Gln Ser Pro Tyr Thr Ala Val Lys Asp Phe Val Ile Val
65                  70                  75                  80

Pro Leu His Thr Thr Pro Glu Thr Ser Val Arg Glu Ile Asp Glu Leu
                85                  90                  95
```

```
Ala Asp Val Tyr Thr Asp Val Lys Arg Arg Trp Asn Ala Glu Asn Phe
            100                 105                 110

Ile Phe Met Gly Asp Phe Asn Ala Gly Cys Ser Tyr Val Pro Lys Lys
        115                 120                 125

Ala Trp Lys Asp Ile Arg Leu Arg Thr Asp Pro Lys Phe Val Trp Leu
    130                 135                 140

Ile Gly Asp Gln Glu Asp Thr Thr Val Lys Lys Ser Thr Asn Cys Ala
145                 150                 155                 160

Tyr Asp Arg Ile Val Leu Arg Gly Gln Asn Ile Val Asn Ser Gly Gly
                165                 170                 175

Pro Gln Ser Asn Leu Val Phe Asp Phe Gln Lys Ala Tyr Arg Leu Ser
            180                 185                 190

Glu Ser Lys Ala Leu
        195
```

<210> SEQ ID NO 3
<211> LENGTH: 671
<212> TYPE: DNA
<213> ORGANISM: Bos sp.

<400> SEQUENCE: 3

```
acaacaggat ctgccccata ctgatggaga agctaaacgg aaattcaaga aaaggcataa    60
catacaacta tgtgattagc tctcgccttg aagaaacac atataaagaa cagtatgcct   120
ttctctataa agaaaagcta gtgtctgtaa acaaagcta cctctaccac gactatcagg   180
ctggagacgc agatgtgttt tccagggaac cctttgtggt ctggttccag tcaccctaca   240
ccgctgtcaa ggacttcgtg attgtccccc tgcacaccac ccctgagaca tccgttagag   300
agattgatga gctggctgat gtctacacag atgtgaaacg tcgctggaat gcagagaatt   360
tcattttcat gggtgacttc aatgctggct gcagctacgt ccccaagaag gcctggaagg   420
acatccgcct gaggacggac cccaagttcg tttggctgat cggggaccaa gaggacacca   480
cggtcaagaa gagcacaaac tgcgcctatg acaggatcgt gcttagagga caaatattg   540
tcaactctgg tggtcctcaa tcaaacctcg tctttgattt ccagaaagct tacaggttgt   600
ctgaatcgaa ggccctggat gtcagcgacc actttccagt tcatcatcat catcatcatg   660
aagaaccatg a                                                        671
```

<210> SEQ ID NO 4
<211> LENGTH: 21
<212> TYPE: DNA
<213> ORGANISM: Artificial Sequence
<220> FEATURE:
<223> OTHER INFORMATION: synthetic DNA

<400> SEQUENCE: 4

```
cgtgaggagc ttcggcgaga g                                              21
```

<210> SEQ ID NO 5
<211> LENGTH: 26
<212> TYPE: PRT
<213> ORGANISM: Bos sp.
<220> FEATURE:
<221> NAME/KEY: misc_feature
<222> LOCATION: (4)..(4)
<223> OTHER INFORMATION: Xaa is any amino acid

<400> SEQUENCE: 5

```
Leu Lys Ile Xaa Ser Phe Asn Val Arg Ser Phe Gly Glu Ser Lys Lys
1               5                   10                  15
```

```
Ala Gly Phe Asn Ala Met Arg Val Ile Val
            20                  25

<210> SEQ ID NO 6
<211> LENGTH: 26
<212> TYPE: DNA
<213> ORGANISM: Artificial Sequence
<220> FEATURE:
<223> OTHER INFORMATION: synthetic DNA

<400> SEQUENCE: 6
acaacaggat ctgccccata ctgatg                                  26

<210> SEQ ID NO 7
<211> LENGTH: 25
<212> TYPE: DNA
<213> ORGANISM: Artificial Sequence
<220> FEATURE:
<223> OTHER INFORMATION: synthetic DNA

<400> SEQUENCE: 7
tcaactggaa agtggtcgct gacat                                   25

<210> SEQ ID NO 8
<211> LENGTH: 27
<212> TYPE: DNA
<213> ORGANISM: Artificial Sequence
<220> FEATURE:
<223> OTHER INFORMATION: synthetic DNA

<400> SEQUENCE: 8
acaacaggat ctgccccata ctgatgg                                 27

<210> SEQ ID NO 9
<211> LENGTH: 57
<212> TYPE: DNA
<213> ORGANISM: Artificial Sequence
<220> FEATURE:
<223> OTHER INFORMATION: synthetic DNA

<400> SEQUENCE: 9
tcatggttct tcatgatgat gatgatgatg aactggaaag tggtcgctga catccag    57
```

ISOLATED POLYNUCLEOTIDE SEQUENCES ENCODING A FERTILITY ASSOCIATED ANTIGEN

CROSS-REFERENCE TO RELATED APPLICATION

The present invention claims priority to U.S. Provisional Application No. 60/218,140 filed Jul. 14, 2000, the entire contents of which are incorporated herein by reference.

BACKGROUND OF THE INVENTION

1. Field of the Invention

The present invention provides an isolated polynucleotide sequence and amino acid sequence of the bovine fertility associated antigen, methods of producing recombinant bovine FAA, and methods of increasing the stability of a sperm or fertility of a mammal.

2. Discussion of the Background

It has been well-documented that seminal fluid is a complex mixture consisting of secretions of the male accessory organs of reproduction: seminal vesicles (V.G.), prostate (P.G.), and bulbourethral glands (B. G. Shivaji et al., 1990). Of the seminal fluid constituents, some have been shown to inhibit (Davis, 1976; Lenz et al., 1982) and others to stimulate (Florman and First, 1988; Miller et al., 1990; Therien et al. 2001 [Biology of Reproduction 65:41–51, 2001]) sperm capacitation in vitro.

Seminal components that stimulate capacitation include a family of heparin-binding proteins (HBP) that bind to sperm ejaculation and convey heparin-induced capacitation (Miller, 1990). A murine monoclonal antibody (mAb), M1, generated by immunization with purified HBP, recognized three distinct proteins in immunoblots of bovine sperm extracts (Bellin et al., 1996, 1998). One of the three HBPs was apparent to be a single 31-kDa mass and was described as fertility-associated antigen (FAA; Bellin et al., 1998). The polynucleotide coding sequence for HBP designated as FAA, and the amino acid sequence of FAA, are distinctly different from other seminal proteins without or with heparin-binding activity described by others (e.g., Manjunanth et al., 1987; Shivaji et al., 1990; Calvete et al., 1996; Therien et al., 2001)

SUMMARY OF THE INVENTION

One object of the present invention is isolated polynucleotides which encode a non-human fertility associated antigen (FAA). One embodiment of such a polynucleotide is shown in SEQ ID NO:1

Another object of the present invention is a vector comprising these isolated polynucleotides, and host cells comprising these isolated polynucleotides.

Another object of the present invention is a method of producing a recombinant bovine FAA by introducing a recombinant polynucleotide encoding FAA into a host cell; culturing said host cell under conditions suitable for expression of the recombinant bovine FAA; and isolating the FAA produced.

Another object of the present invention is a method to increase the stability of the plasma membrane plus acrosome of a sperm cell, comprising administration of the recombinant FAA of the invention to sperm cells. In one embodiment of the invention, the sperm cell is a mammalian sperm cell and preferably the mammal is a cow, although the polypeptide and methods described should induce similar changes in sperm from buffalo, horses, pigs, sheep, and even human. In another embodiment the sperm cell is an avian sperm cell, preferably chicken or turkey sperm cells.

Another object of the present invention is a method of increasing the fertility of mammals or avians by mixing the FAA of the invention with sperm from said mammal or avian. Said mixing can be accomplished in vitro and involve either: (1) neat semen from said male and said FAA; or (2) isolated, washed or extended sperm from said male and said FAA. Alternatively, fertility might be increased after depositing said FAA alone, or as FAA in a carrier selected to improve retention of said FAA, retention of bioactivity or mixing with sperm, into the reproductive tract of a female mammal where it would mix with any sperm subsequently deposited into said reproductive tract. In one embodiment of the invention, the mammal is cattle, but the methods described should be equally applicable in buffalo, horses, pigs, or sheep, even human. With respect to avians, chickens or turkeys are preferred embodiments.

Another object of the present invention is production of a transgenic non-human mammal with the isolated bovine polynucleotide as described herein that encodes bovine FAA.

The above objects highlight certain aspects of the invention. Additional objects, aspects and embodiments of the invention are found in the following detailed description of the invention.

DETAILED DESCRIPTION OF THE INVENTION

Figure 1:
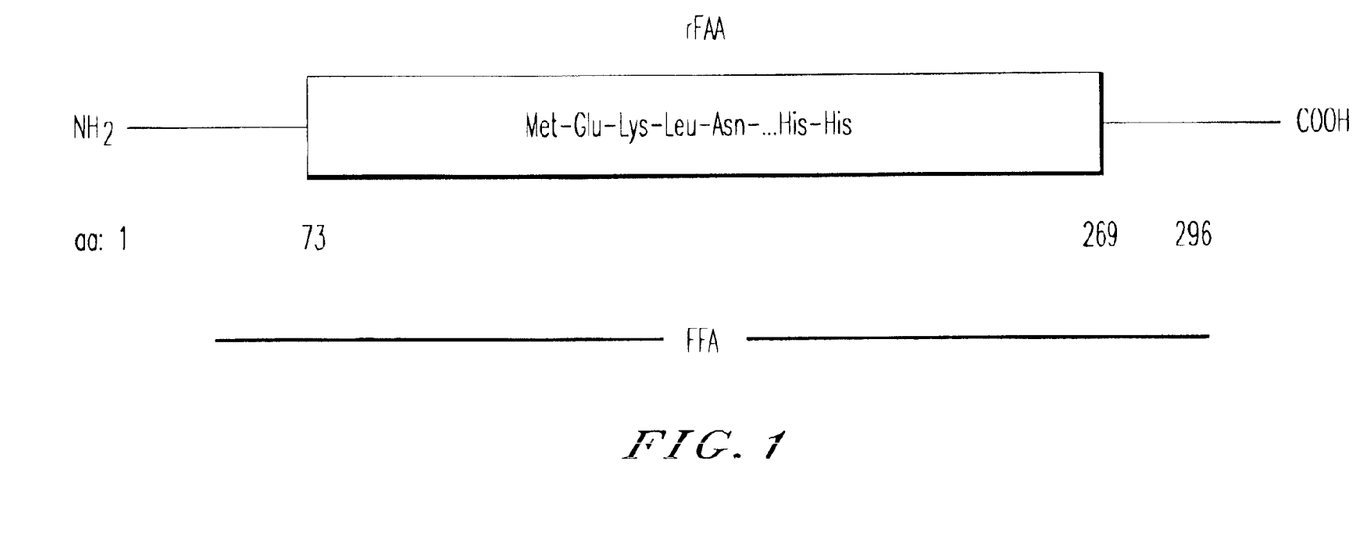
FIG. 1: Depicted recombinant bovine FAA (rFAA) (SEQ ID NO:11), produced from cloned partial cDNA of bovine FAA gene in *E. coli*, showing the comparative position of the segment corresponding to natural intact bovine FAA.
Figure 2:
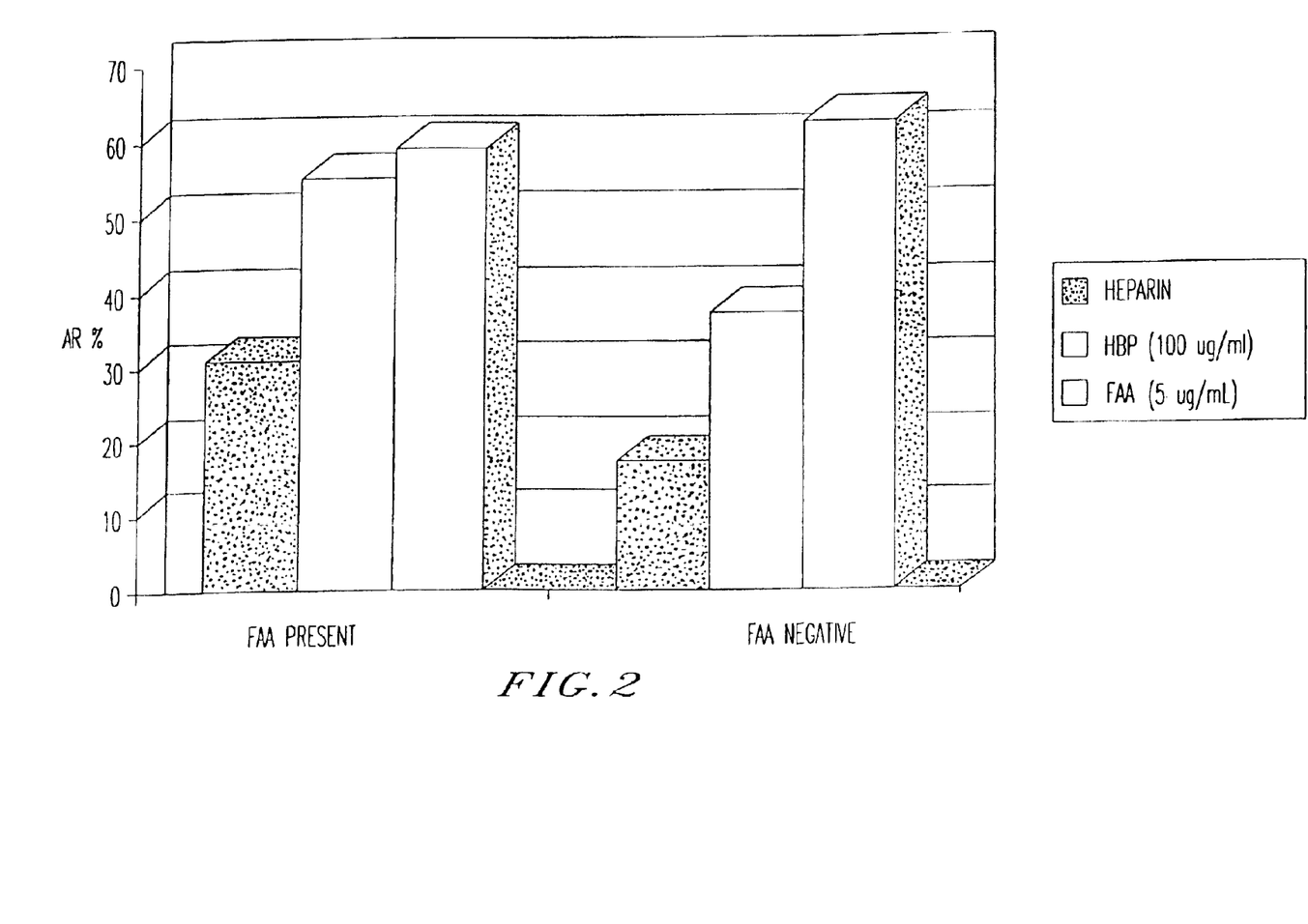
FIG. 2: Percent increase in acrosome reaction for each treatment above the control level. Natural FAA was extracted from a sperm sample of a fertile bull with detectable FAA on sperm and FAA-negative material was similarly extracted from sperm sample of a non-fertile bull without detectable FAA on sperm. The fertile bull (FAA present) reacted better to heparin induction of capacitation/acrosome reactions. Addition of FAA (5 $\mu$g/ml) stimulated maximum increase of acrosome reactions for each bull.
Figure 3:
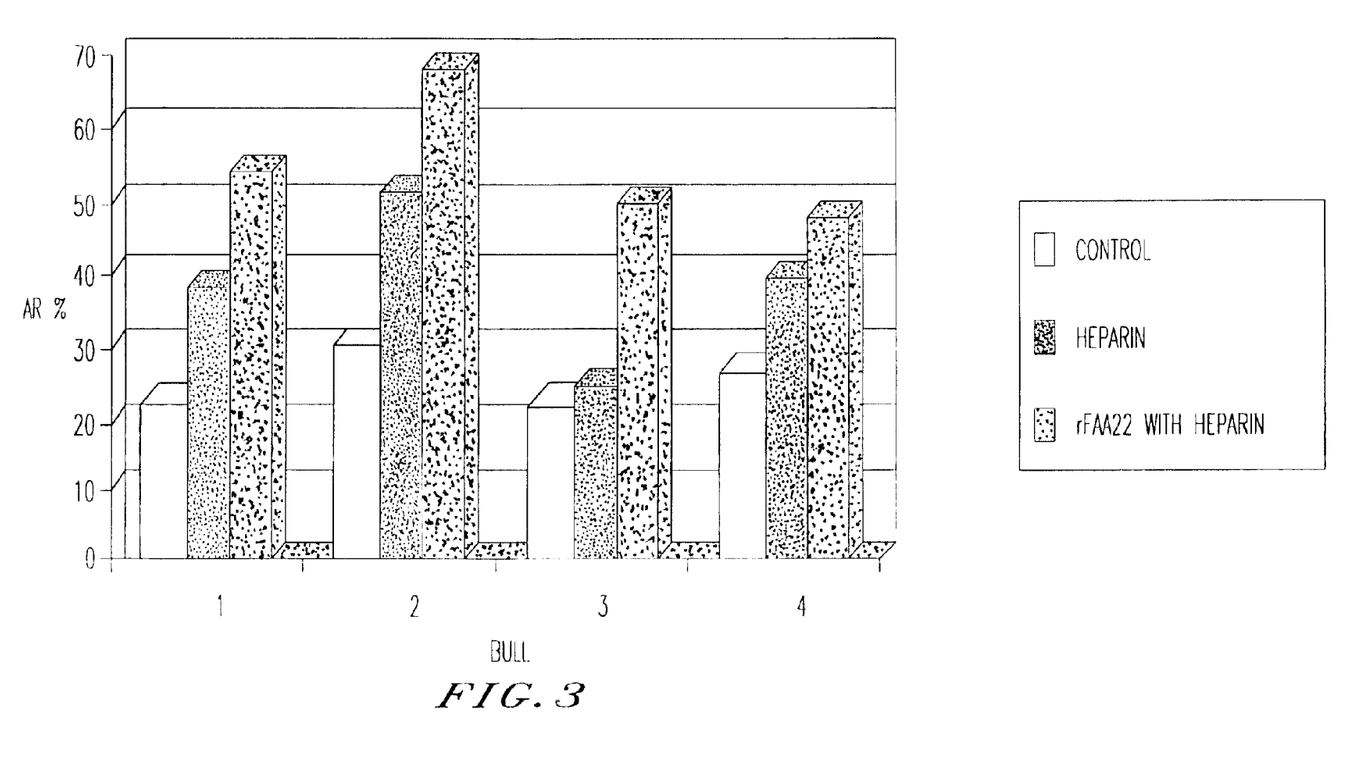
FIG. 3: Effects of heparin alone (10 $\mu$g/ml) or the 22 kDa recombinant bovine FAA (rFAA, 20 $\mu$g/ml) with heparin to stimulate acrosome reaction in washed sperm. Data replicated with sperm from four fertile bulls.
Figure 4:
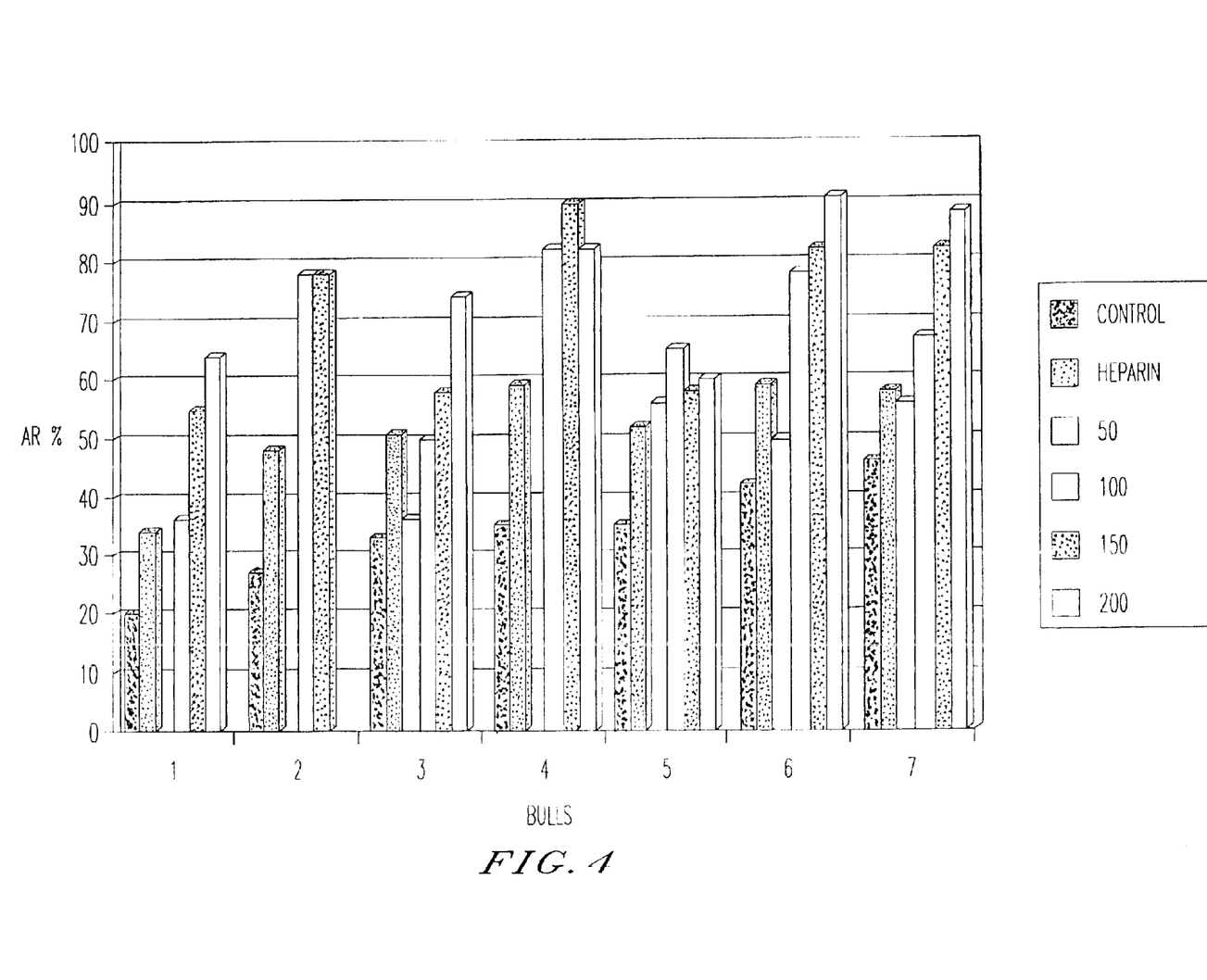
FIG. 4. Dose-response comparisons ($\mu$g/ml) of the 22 kDa recombinant bovine FAA (rFAA) added with heparin (10 $\mu$g/ml) to washed sperm. Each data point represents the average for two to five ejaculates from each bull.
Figure 5:
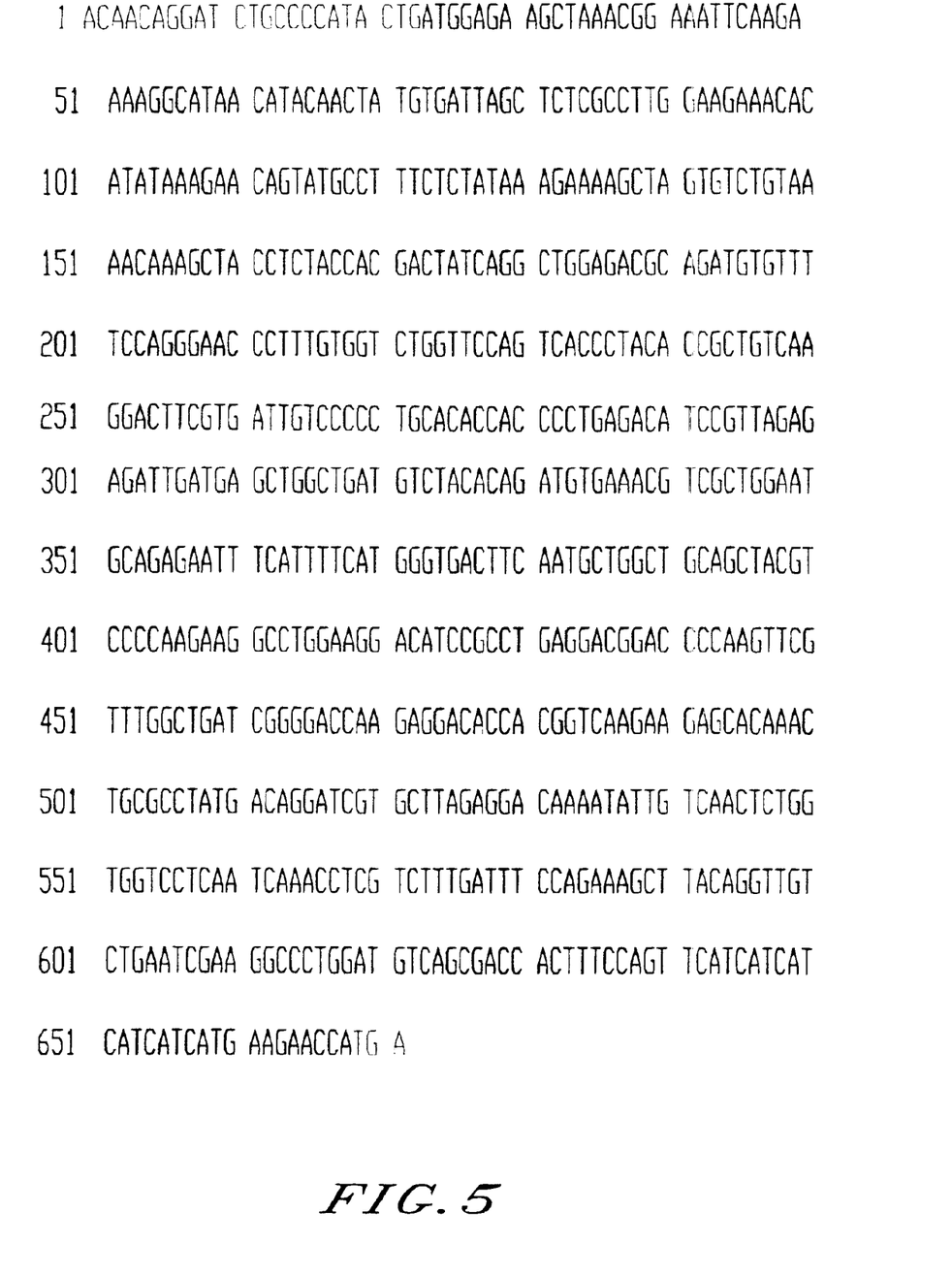
FIG. 5. Coding sequence for the 22 kDa recombinant FAA (rFAA) (SEQ ID NO:3).
Figure 6:
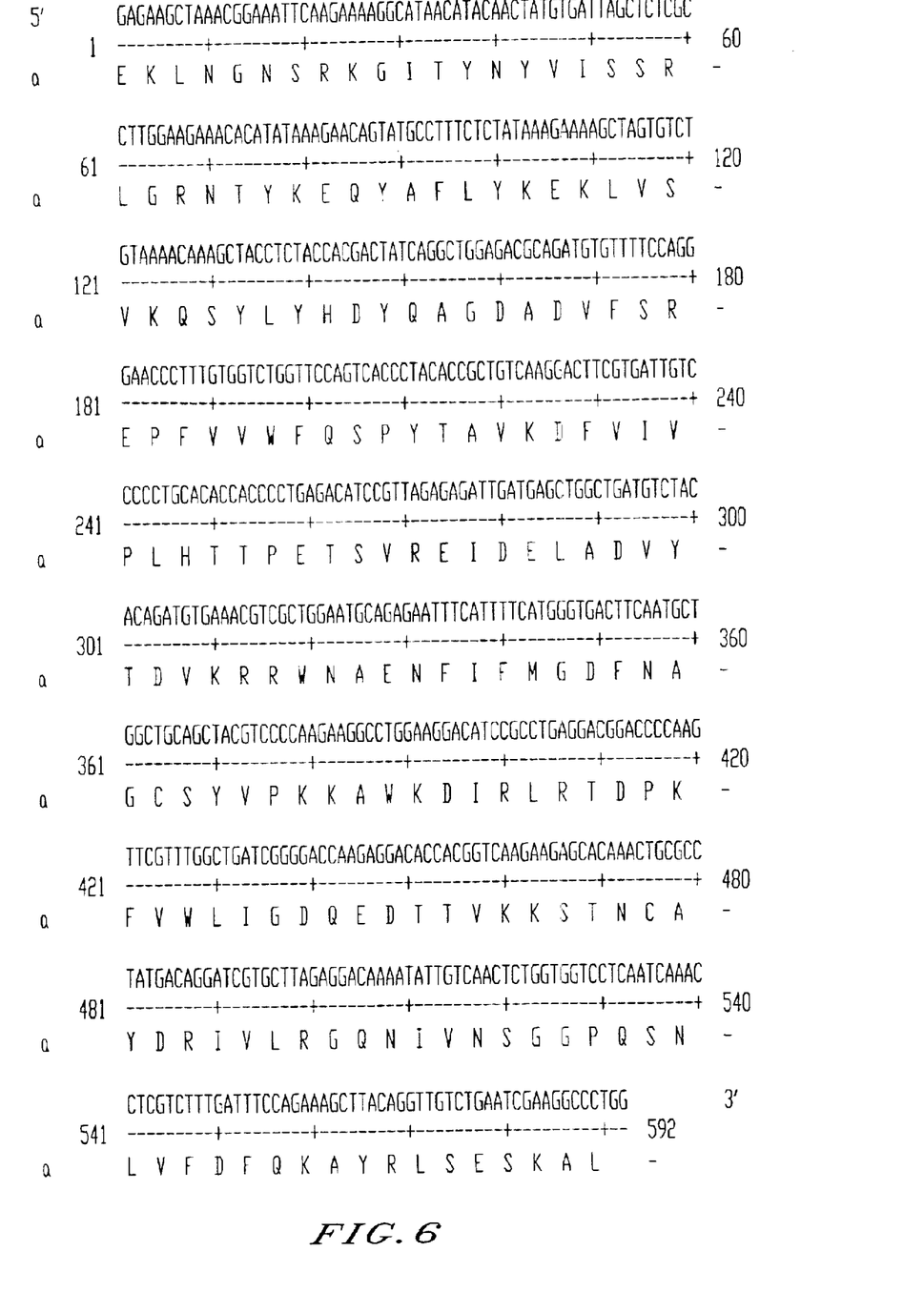
FIG. 6. Partial cDNA sequence of bovine FAA (SEQ ID NO:1) and its deduced amino acid sequence (SEQ ID NO:2).

Terms and general procedures used herein:

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins which comprise two or more amino acids bonded via peptide bonds. In particular, the term refers to polypeptides with the biological activity of FAA, and also those which are at least 70%, preferably at least 80% and more preferably at least 90% to 95% identical to the polypeptide according to SEQ ID NO:2 and have the activity mentioned. Included within the scope of the present invention are polypeptide fragments of SEQ ID NO:2 or those which are identical as described herein, which posses the activity of FAA as described herein.

Polynucleotides which encode the FAA as used herein is understood to mean the sequences exemplified in this application as well as those sequences which have substantial identity to SEQ ID NO:1 and which encode a molecule having one or more of the bioactivities of natural FAA. Preferably, such polynucleotides are those which are at least 70%, preferably at least 80% and more preferably at least 90% to 95% identical to SEQ ID NO:1 or SEQ ID NO:3.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl (Anal. Biochem., 138:267–284, 1984): $T_m$=81.5° C.+16.6 (log M)+0.41 (% GC)–0.61 (% form)– 500/L; where M is the molari monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with approximately 90% identity are sought, the $T_m$ can be decreased 10° C.

Generally, stringent conditions are selected to be about 5° C. lower than the thermal melting point ($T_m$) for the specific sequence and its complement at a defined ionic strength and pH. However, severely stringent conditions can utilize hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

Accomplishment of this invention required polynucleotides which hybridize under stringent conditions to the cDNA encoding bovine FAA. Stringent hybridization conditions are understood to mean those conditions where hybridization, either in solution or on a solid support, occur between two polynucleotide molecules which are 70% to 100% homologous in nucleotide sequence which include 75%, 80%, 85%, 90%, 95%, 98% and all values and subranges therebetween. Methods of stringent hybridization are known in the art which conditions can be calculated by means known in the art. This is disclosed in Sambrook et al., Molecular Cloning: A Laboratory Manual, $2^{nd}$ Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of DNA sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Suitable vectors for carrying the cDNA of the bovine FAA gene include those vectors which can direct expression of the gene in bacterial, yeast, mammalian and/or insect cells as known in the art. One embodiment of the present invention is whereby the vectors contain an inducible or otherwise regulated expression system whereby the bovine FAA cDNA may be expressed under certain conditions and not expressed under other conditions. Examples of such vectors and suitable cells in which they can be introduced are described in Sambrook et al., *Molecular Cloning: A Laboratory Manual*, $2^{nd}$ Ed., Cold Spring Harbor Laboratory Press, 1989, Cold Spring Harbor, N.Y. and *Current Protocols in Molecular Biology*, Ausebel et al, eds., John Wiley and Sons, Inc., 2000, the contents of which are herein incorporated by reference. Methods of introducing the cDNA or vector containing the cDNA include calcium mediated transfection, liposomes, electroporation, transformation and infection when the cDNA is contained in a viral vector as known in the art. These and other methods are described in Sambrook et al., *Molecular Cloning: A Laboratory Manual*, $2^{nd}$ Ed., Cold Spring Harbor Laboratory Press, 1989, Cold Spring Harbor, N.Y. and *Current Protocols in Molecular Biology*, Ausebel et al, eds., John Wiley and Sons, Inc., 2000.

Suitable culture conditions for the growth and/or production of the recombinant FAA are dependent on the cell type used. Examples of culture conditions for various cells is described in Sambrook et al., *Molecular Cloning: A Laboratory Manual*, $2^{nd}$ Ed., Cold Spring Harbor Laboratory Press, 1989, Cold Spring Harbor, N.Y.; *Current Protocols in Molecular Biology*, Ausebel et al, eds., John Wiley and Sons, Inc., 2000; and *Cells: A Laboratory Manual* (Vols. 1–3), Spector et al, eds., Cold Spring Harbor Laboratory Press, Cold Spring Harbor, N.Y., 1988.

Methods of purifying FAA include high performance liquid chromatography (HPLC), ion-exchange chromatography, size exclusion chromatography; affinity separations using materials such as beads with exposed heparin, metals, or lipids; or other approaches known to those skilled in the art. These and other methods of protein purification are disclosed in Sambrook et al., *Molecular Cloning: A Laboratory Manual*, $2^{nd}$ Ed., Cold Spring Harbor Laboratory Press, 1989, Cold Spring Harbor, N.Y.; *Current Protocols in Molecular Biology*, Ausebel et al, eds., John Wiley and Sons, Inc., 2000 and *Protein Purification*, Scopes and Cantor, eds., Springer-Verlag, 1994 which are incorporated herein by reference.

The Starting Point:

It was known (Sprott et al., 2000; Bellin et al., 1994, 1998) that presence of FAA on bull sperm was associated with 16–19% higher fertility of such bulls used for artificial insemination or natural service than fertility obtained with bulls whose sperm have no detectable FAA. We found (McCauley et al., 1999) that FAA could be extracted from bull sperm and separated from rest of the HBP complexes by reverse-phase high performance liquid chromatography (RP-HPLC). FAA eluted as a very hydrophobic peptide. Determination of the polynucleotide sequence, preparation of recombinant DNA coding for the recombinant bovine FAA, and evaluation of the biological responses of sperm involved linking numerous steps, with procedures detailed above, in an innovative manner and inclusion of other novel steps to complete the invention disclosed herein.

Extraction of Total RNA Containing the Message RNA for Bovine FAA:

Bovine accessory sex glands (bulbourethral gland, prostate, and seminal vesicles) were obtained immediately after slaughter. Total RNA was isolated following a modified protocol (Bonham and Danielpour, 1996). Briefly, one gram of fresh tissue from each gland was placed in 10 mL of solution D (4 M guanidinium thiocyanate, 25 mM sodium acetate, pH 7.0, 5% N-lauroylsarcosine, 0.1 M 2-mercaptoethanol). The sample of each gland was homogenized, and then chilled on ice while adding 0.1 vol 2 M NaAc (pH 4.0), 1 vol water-saturated phenol, and 0.2 vol of chloroform isoamyl alcohol (49:1). After incubating on ice for 15 min, samples were centrifuged at 10,000×g for 20 minutes at room temperature. The aqueous phase was transferred to a new tube containing an equal volume of isopropanol, incubated at −20° C. for 1 hour, and centrifuged at 10,000×g for 20 minutes at 4° C. to precipitate total RNA. The resulting RNA pellet was suspended into 0.3 volumes of solution D and an equal volume of cold ethanol, transferred to a RNeasy column (Qiagen Inc., Chatsworth, Calif.), and centrifuged at 8,000×g for 15 sec. Total RNA was eluted with 100 $\mu$L of DEPC-treated sterile distilled water.

3' Rapid Amplification of cDNA Ends and Reverse Transcriptase Polymerase Chain Reaction:

First strand cDNA synthesis was catalyzed by SuperScript™ II RNase H RT (GibcoBRL, Grand Island, N.Y.) templated with total RNA extracted from each bovine accessory gland. Five $\mu$g of RNA from each gland were mixed with 500 nM adaptor primer (5'-GGC CAC GCG TCG ACT AGT ACT T(16)-3', GibcoBRL SEQ ID NO:10), heated to 70° C. for 10 min, chilled on ice for 1 min, followed by addition of 20 mM Tris-Cl (pH 8.4), 50 mM KCl, 2.5 mM $MgCl_2$, 10 mM DTT, and 500 $\mu$M each of dATP, dTTP, dCTP, dGTP for a final volume of 20 $\mu$l. This mix was incubated at 42° C. for 50 min with 200 units of SuperScript II RT, and terminated at 70° C. for 15 min. Two units of RNase H were added and the mixture was incubated for 20 min at 37° C. to remove the RNA strand of the cDNA:RNA hybrid molecule. First strand cDNA products were used as templates to isolate and amplify the cDNA segments of the bovine FAA gene. The isolation and identification of the cDNA of bovine FAA gene was accomplished by a series of attempts, initiated by a 3' rapid amplification of cDNA ends (3' RACE) following a commercial protocol (Cat. NO. 18373-019, GibcoBRL) with a gene specific primer (CGT GAG GAG CTT CGG CGA GAG (SEQ ID NO:4) designed based on a N-terminal peptide sequence (LKIXSFNVRSFGESKKAGFNAMRVIV (SEQ ID NO:5)), which was conceived in our laboratory. Based on the 3' RACE product sequences and a published human cDNA sequence (Rodriguez et al., 1997), which was in high homology to the 3' RACE product sequences, new PCR primers were designed to re-amplify the cDNA of bovine FAA gene. The new PCR mix consisted of 50 ng of the first strand cDNA, 20 mM Tris-Cl (pH 8.3), 50 mM KCl, 1.5 mM $MgCl_2$, 200 $\mu$M each of dNTP (dATP, dTTP, dCTP, dGTP), 400 nM of the new gene specific primers (5' primer: ACA ACA GGA TCT GCC CCA TAC TGA TG (SEQ ID NO:6), 3' primer: TCA ACT GGA AAG TGG TCG CTG ACA T (SEQ ID NO:7)), and 0.5 unit of Taq DNA polymerase in a final volume of 20 $\mu$l. PCR conditions were 1 min at 94° C., 1 min at 58° C., and 1 min at 72° C. for 35 cycles, followed by a final extension step of 72° C. for 30 min.

Cloning of the RT-PCR Product and cDNA Sequence Analysis:

The fresh PCR products were immediately cloned into the pCR2.1-TOPO vector (Cat NO. k45001-01, Invitrogen) following the manufacturer's instruction. DNA was extracted from the positive clones, air-dried, and re-suspended in sterile distilled water at a final concentration of 0.2 $\mu$g/$\mu$l. Sequence analysis of the inserted RT-PCR products was performed (Applied Biosystems 373 A Automated DNA sequencer utilizing the DyeDeoxy™ terminator chemistry) for each of the clones and for both strands of the inserted DNA. Validation of the cDNA sequence of the bovine FAA gene was confirmed by analysis of alignments between the deduced peptide sequence of the cloned cDNA and additional two pieces of N-terminal amino acid sequences of internal peptides (a 20mer and a 15mer, data not shown), which were generated by lys-C digestion of purified bovine seminal FAA.

Establishment of the Bovine Recombinant FAA Clones:

The partial bovine FAA cDNA isolated, identified and validated by 3' RACE, RT-PCR, cloning and sequence analyses, was re-cloned into the pCR® T7/CT-TOPO Expression Vector (Cat. NO. K4210-01, Invitrogen) following the manufacturer's instruction. The insert to establish the recombinant line of clones with the pCR® T7/CT-TOPO Expression Vector was generated by PCR with re-designed primers (5' primer: ACA ACA GGA TCT GCC CCA TAC TGA TGG (SEQ ID NO:8), 3' primer: TCA TGG TTC TTC ATG ATG ATG ATG ATG ATG AAC TGG AAA GTG GTC GCT GAC ATC CAG (SEQ ID NO:9) ) based on the cloned cDNA sequence in pCR2.1-TOPO vectors and our innovation aimed to facilitate the expression of a bio-active recombinant FAA.

Production and Purification of Recombinant Bovine FAA:

Transformed One Shot BL21 (DE3) cells (Invitrogen, San Diego, Calif.) was incubated in LB containing 100 µg/ml ampicillin and 34 µg/ml chloramphenicol at 37° C. for 2 h, induced with IPTG at a final concentration of 0.7 mM, continued incubation for an additional 3 h before harvest. The harvested cells were immediately precipitated to pellet by centrifugation at 3,000×g for 15 min at 4° C. and frozen at −20° C. The pellet was then re-suspended in PBS with 0.6 N KCl, and gently agitated for 60 min at 4° C. The pellet suspension was then centrifuged at 600×g for 10 min, and the supernatant containing the KCl extract was recovered and centrifuged at 14,000×g for 20 min. The clarified supernatant was applied to a heparin-affinity column (heparin Econo-Pac, Bio-Rad, Hercules, Calif.; or heparin-Sepharose CL-6B, Pharmacia [5×250 mm]) connected in-line to a peristaltic pump (ISCO, Inc. Lincoln, Nebr.) at a flow rate of approximately 1 ml/min. The column was equilibrated with 40 mM Tris (pH 7.4), 2 mM $CaCl_2$, 200 µM PMSF, 0.01% $NaN_3$ (TC-A). Peak detection was achieved by monitoring absorbance at 280 nm with an UA-5 absorbance detector (ISCO, Inc. Lincoln, Nebr.). After non-binding proteins had cleared the column and baseline conditions were achieved, recombinant FAA was eluted with 2 M NaCl in TC-A. The fraction containing the recombinant FAA was diluted in TC-A and desalted/concentrated by centrifugation (Beckman J-6M, 2,000 g) in centriprep tubes (Ultrafree-15, 12,000 MWCO, Millipore, Bedford, Mass.). All separations were performed at 4° C. Samples were assayed to determine protein concentration (Bio-Rad Dc protein assay, Bio-Rad, Hercules, Calif.) using bovine serum albumin (BSA) as standard. Desalted fractions were immediately frozen, lyophilized, and stored until further analysis.

The inserted DNA included a 592 base pair segment of the bovine FAA cDNA corresponding to amino acid residues 72 to 269 of the parent protein. The vector of the recombinant bovine FAA is a high-level, inducible plasmid vector expressed in *E. coli*. Recombinant FAA from the transformed *E. coli* cells was further purified using RP-HPLC, following a protocol similar to that used to separate natural FAA from HBP complex. The yield of the rFAA purified by the said protocol is 750 mg/L of LB culture of the recombinant clone. The expressed protein of recombinant bovine FAA contains a total of 215 amino acids. Mass-spectral analysis of the rFAA gave a mass of 22 kDa, which differed from the anticipated rFAA mass based on the amino acid sequence by less than 3%.

Use of Recombinant FAA to Modify Sperm Cells:

From earlier studies, we hypothesized that FAA isolated by HPLC from bovine seminal fluid can increase the capacitation of sperm in intro. We also hypothesized that recombinant FAA produced as disclosed above, could be used to stabilize sperm membranes and also increase fertility. We further hypothesized that the response to recombinant FAA would be greater for subfertile mammals than for fertile mammals. To provide the examples herein, we used cattle because sperm can be collected easily and fertility can be established, by methods known to those skilled in the art. However, changes documented herein, and other undocumented changes, with cattle sperm are likely to occur in sperm from buffalo, horses, mice, pigs, sheep, and even human. Preferred embodiments of the invention utilize these species, but use with other mammals, chickens, or turkeys would be equally appropriate.

The present invention provides a method of stabilizing sperm cells by treating the sperm with FAA and/or heparin, and/or HBP, either for cold storage or other means of storing sperm that are commonly used in the art. Often, sperm from a subfertile mammal will have little or no FAA present. By using supplemental recombinant FAA to modify the plasma plus acrosome membranes of sperm, the fertility of the mammal is increased because FAA: (1) initially stabilizes the sperm cells, reducing death or decline in function; and (2) later facilitates the capacitation of individual sperm within the female reproductive tract, a step obligatory for fertilization. The recombinant FAA can be administered alone, or in combination with heparin and/or heparin binding protein, or together with other molecules. The recombinant FAA treatment can comprise mixing in vitro said FAA with either: (1) neat semen from a mammalian male; or (2) isolated, washed or extended sperm from a mammalian male. An preferred procedure would be to mix neat semen, or sperm liberated from the excurrent ducts, with recombinant FAA before further processing of said semen or sperm in an extender appropriate for storage at 4–25° C. or at cryogenic temperatures (e.g., −196° C.).

Alternatively, said modification of the plasma plus acrosome membranes of sperm and resultant increase in fertility might accomplished by depositing said FAA alone, or as FAA in a carrier selected to improve retention of said FAA, retention of bioactivity or mixing with sperm, into the reproductive tract of a female mammal where it would mix with any sperm subsequently deposited into said reproductive tract. In one embodiment of the invention, the mammal is cattle, but the methods described should be equally applicable in buffalo, horses, pigs, or sheep, and even human.

Another means to modify sperm and increase fertility is to introduce an expression vector containing the FAA cDNA directly into the animal (i.e., treatment), whereby the in vivo expression of the cDNA results in FAA binding to the sperm during admixture with seminal plasma at ejaculation, in the case of treated male mammals, or after sperm are deposited in the female tract during natural mating or artificial insemination, in the case of treated female mammals. Such transgenic mammals and, in particular, transgenic cattle containing the FAA cDNA or recombinant cDNA of the FAA are included within the present invention.

The effect of rFAA on the proportion of acrosome reacted sperm, a measure of stabilization of the plasma plus acrosomal membranes, was evaluated. Freshly ejaculated sperm were diluted and suspended at one billion sperm/ml in modified Tyrode's (TALP, Sigma) buffer containing 10 μg heparin and 0 μg rFAA/ml of neat semen (control) or 10 μg heparin and 200 μg rFAA/ml of neat semen (treated). The sperm suspensions incubated 4 hours at 37° C. to allow capacitation, which is necessary for a spermatozoon to undergo the acrosome reaction. Within 30 min, rostral portions of 200 sperm per sample were evaluated for changes characteristic of the acrosome reaction, by phase contrast microscopy at 1000× (Leica Diplan microscope). Acrosome-reacted sperm were characterized by a loosening or loss of the acrosome and overlying plasma membrane, where as in sperm not having undergone the acrosome reaction the acrosome was not swollen and the plasma membrane over the rostral sperm head remained intact.

EXAMPLE 1

It was known that bovine sperm can be capacitated with heparin in vitro, leading to an increase in percentage of acrosome-reacted sperm over time. Semen was obtained from a fertile beef bull (approximately 65% pregnancy rate in natural service) and also a subfertile beef bull ( approximately 48% pregnancy rate) and diluted in TALP buffer as above. In this trial, 0.5 ml aliquants of each sperm suspension contained 0, 1, or 5 μg/ml of FAA purified by RP-HPLC in combination with 0, 20, 50 or 100 μg/ml of a crude extract of native HBP, and 0 or 200 μg/ml of heparin (Protein Scientific Lab, Madison, Wis.) as detailed in Table 1. The trial was replicated using three ejaculates from each bull.

Inclusion of either 1 μg FAA/ml or 100 μg native HBP/ml , in addition to 200 μg heparin/ml, increased the percentage of acrosome reacted sperm by >45% (P<0.05; 54 vs 34% and 71 vs 48% acrosome reacted sperm for the subfertile and fertile bulls). The incidence of spontaneous acrosome reactions was 17% for both bulls. Use of 5 μg FAA/ml was not substantially more effective than 1 μg FAA/ml (Table 1). We concluded that the FAA substantially modified the process of capacitation in vitro, as hypothesized.

EXAMPLE 2

It is customary to use cryopreserved sperm for artificial insemination (AI) of cattle, and other species, including buffalo, horses, humans, and sheep. Given that exposure of sperm to purified FAA altered the percentage of heparin-induced capaciation of sperm in Example 1, we hypothesized that exposure of sperm to rFAA before processing and freeze-thawing would reduce cryo-damage to the sperm. We further hypothesized that this would be evident as a reduced incidence of spontaneous acrosome reactions, common in thawed sperm, and increased fertility of sperm exposed to rFAA before cryopreservation.

Fresh ejaculates from seven bulls, known to represent a range in fertility, were split evenly, one half of each sample was treated with 0 μg (control) rFAA and the other half was treated with 200 μg (treated) rFAA/ml of neat semen, and both control and the treated semen samples were incubated at room temperature for 15 minutes prior to routine processing of freezing. The semen was packaged into 0.5 ml straws and frozen at −196° C., with a procedure conventional to the cattle industry. Straws of semen were stored in liquid nitrogen until thawed, in a random manner across bulls and treatments. The contents of 2 straws were pooled in a vial and incubated at 37° C. for 3 hours. The number of sperm with an altered acrosome (i.e., false acrosome reaction shortly after thawing) or having undergone a true acrosome reaction were evaluated at 0, 1, 2 and 3 hours after thawing, using a microscope interference-contrast optics. Straws representing each bull-treatment combination were thawed and evaluated on three separate occasions; data were averaged (Table 2).

In control samples (no rFAA), the percentage of sperm with an intact acrosome after the freeze-thaw process ranged from 35 to 82% with a mean value of 54%. The percentage of sperm with an intact acrosome for treated samples (with rFAA) ranged from 54 to 87% with a mean value of 87% (Table 2). Increased stabilization of the sperm plasma membrane plus acrosome system resulted from incubation with 200 μg rFAA/ml before freezing. The differences of intact acrosome percentages between the control and the treated values ranged from 0 up to 30 percentages with an average of 18.3 percentage units. The differences are statistically significant (P<0.01). We concluded that addition of rFAA to partially extended semen beneficially modified the sperm in a manner enhancing retention of a normal acrosome system through freeze-thawing. Apparently, the rFAA on or in proximity to sperm reduced the incidence of capacition caused by the high salt concentrations associated with freeze-thawing, improved membrane stability, and improved the percentage of sperm with a normal acrosome. We further concluded that the response to the said recombinant FAA treatment would be greater for subfertile mammals than for fertile or highly fertile mammals, supported by the responses of the subfertile Bulls A and B (incceases of intact acromsome of 27 and 30%) versus the fertile bulls F and G (increases of 16 and 0%, respectively, Table 2).

EXAMPLE 3

The percent of intact acrosomes in a semen sample post-thaw is the trait most highly correlated with fertility (Saacke and white, 1972). Preliminary data (Table 3) from an independent commercial company's trial suggested that fertility of bulls whose sperm were treated as above with the said rFAA was higher than fertility of bulls whose sperm were not, measured by non-return rates.

The recombinant FAA (rFAA) was added directly to split ejaculates of neat semen of small group of bulls at a dose of 0 μg rFAA/ml of neat semen (control) for one half the split, and of 200 μg rFAA/ml of neat semen (treated) for the other half of the split before the semen samples were subjected to their initial 1:3 extension. Samples were filed into 0.5 ml straws and processed in the routine manner for subsequent A.I. On subsequent days, straws of both splits (control and treated) were thawed and incubated for 3 hours in water bathes before A.I. A random group of 200 cows was artificially inseminated with the semen of no rFAA treatment (control), and another random group of 200 cows was inseminated with the semen containing 200 μg rFAA/ml of neat semen (treated). The average 60 day non-return rate of the control group was 32%, and the treated group was 39% (Table 3). We concluded that the said rFAA when used as semen additives increased fertility of bulls, as hypothesized above.

TABLE 1

Stimulation of heparin-induced capacitation of sperm with heparin binding protein (HBP) and Fertility Associated Antigen (FAA) peptide by HPLC. Capacitation was determined by measuring the percent of acrosome reacted sperm (AR %). Semen was obtained from a subfertile bull with non-detectable FAA on sperm and a fertile bull with detectable FAA on sperm. At least three ejaculates for each bull were tested and the assays were conducted in duplicate. A total of 600 sperm cells were examined for each data point. The variation for each treatment was less than 10% of the mean.

| SUBFERTILE BULL WITHOUT FAA ON SPERM | | | | | FERTILE BULL WITH FAA ON SPERM | | | | |
|---|---|---|---|---|---|---|---|---|---|
| Treatment µg/ml | | | Acrosome Reaction | | Treatment (µg/ml) | | | Acrosome Reaction | |
| Heparin | HBP | FAA | % | Change | Heparin | HBP | FAA | % | Change |
| 0 | 0 | 0 | 17 | — | 0 | 0 | 0 | 17 | — |
| 200 | 0 | 0 | 34 | 17 | 200 | 0 | 0 | 48 | 31 |
| 200 | 20 | 0 | 34 | 17 | 200 | 20 | 0 | 44 | 27 |
| 200 | 50 | 0 | 46 | 29 | 200 | 50 | 0 | 66 | 49 |
| 200 | 100 | 0 | 54 | 37 | 200 | 100 | 0 | 72 | 55 |
| 200 | 0 | 1 | 55 | 38 | 200 | 0 | 1 | 70 | 53 |
| 200 | 0 | 5 | 62 | 45 | 200 | 0 | 5 | 76 | 59 |

TABLE 2

The percent intact acrosomes three hours after thawing of processed and frozen sperm samples. Acrosome integrity indicates increased fertility potential. Sperm were treated with 200 µg/ml of rFAA-22 for 15 minutes prior to processing for freezing. Post-thaw intact acrosomes (live sperm) were determined 3 hours after samples were thawed. Sperm were evaluated after 3 separate semen collections and processing for each bull. Standard error of the assay was less than 10 percent.

| INTACT ACROSOMES (%) THREE HOURS POST THAWING OF PROCESSED SEMEN SAMPLES | | | | | | | |
|---|---|---|---|---|---|---|---|
| Treatment | Bull A[1] | Bull B[1] | Bull C | Bull D | Bull E | Bull F | Bull G |
| Control | 35 | 38 | 45 | 60 | 65 | 66 | 82 |
| rFAA-22 | 62 | 68 | 54 | 84 | 87 | 82 | 82 |
| Difference | 27 | 30 | 9 | 24 | 22 | 16 | 0 |

[1]Bulls whose semen had failed a similar 3-hour stress test routinely employed by the bull stud.

TABLE 3

Preliminary trial data showing that applying 200 µg bovine rFAA/ml of neat semen as additives to one half of fresh ejaculates of semen sample of bulls increased fertility comparing to other half of semen sample used in artificial insemination.

| Treatments | A.I. Cows | Non-return Rate |
|---|---|---|
| Control (no rFAA) | 200 | 32% |
| Treated (200 µg rFAA/ml) | 200 | 39% |

What is claimed is:

1. An isolated polynucleotide sequence comprising SEQ ID NO:1 or SEQ ID NO:3.

2. The isolated polynucleotide of claim 1, which comprises SEQ ID NO:1.

3. The isolated polynucleotide of claim 1, which comprises SEQ ID NO:3.

4. The isolated polynucleotide of claim 1, which encodes a fertility associated antigen.

5. A vector comprising the isolated polynucleotide of claim 1.

6. The vector of claim 5, wherein said vector is a prokaryotic expression vector, wherein the vector comprises a bacterial T7 promoter.

7. An isolated host cell comprising the isolated polynucleotide of claim 1.

8. The host cell of claim 7, which is a bacterial cell, a yeast cell or a mammalian cell.

9. A method of producing a fertility associated antigen comprising introducing the isolated polynucleotide of claim 1 into a host cell; culturing said host cell under conditions suitable for expression of fertility associated antigen; and isolating the fertility associated antigen produced.

10. The method of claim 9, wherein said isolating comprises purifying said fertility associated antigen.

11. The method of claim 10, wherein said purifying comprises chromatography and/or affinity separation.

12. The method of claim 9, wherein said host cell is a bacterial cell.

13. The method of claim 9, wherein said host cell is a yeast cell.

14. The method of claim 9, wherein said host cell is a mammalian cell.

* * * * *